(12) United States Patent
Chen et al.

(10) Patent No.: US 8,501,490 B2
(45) Date of Patent: Aug. 6, 2013

(54) BIOASSAYS BASED ON POLYMERIC SEQUENCE PROBE

(75) Inventors: Yong Chen, Sherman Oaks, CA (US);
Suxian Huang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 537 days.

(21) Appl. No.: 12/763,134

(22) Filed: Apr. 19, 2010

(65) Prior Publication Data

US 2011/0171740 A1    Jul. 14, 2011

Related U.S. Application Data

(60) Provisional application No. 61/293,477, filed on Jan. 8, 2010.

(51) Int. Cl.
*G01N 33/50* (2006.01)
*G01N 33/00* (2006.01)
*C07H 21/04* (2006.01)
*C12P 19/34* (2006.01)

(52) U.S. Cl.
USPC ............... 436/94; 436/93; 436/91; 435/91.2; 435/91.1; 435/89; 435/85; 435/72; 435/41; 536/24.3; 536/23.1; 536/22.1; 536/18.7; 977/744; 977/773; 977/700

(58) Field of Classification Search
USPC .............. 436/94, 93, 91; 435/91.2, 91.1, 435/89, 85, 84, 72, 41; 536/24.3, 23.1, 22.1, 536/18.7, 1.1; 977/774, 773, 700
See application file for complete search history.

(56) References Cited

U.S. PATENT DOCUMENTS

| | | | |
|---|---|---|---|
| 5,175,270 | A | 12/1992 | Nilsen et al. |
| 5,635,352 | A | 6/1997 | Urdea et al. |
| 2002/0192649 | A1 | 12/2002 | Lizardi |
| 2006/0223098 | A1 | 10/2006 | Lane et al. |
| 2006/0286583 | A1 | 12/2006 | Luo et al. |
| 2008/0038725 | A1 | 2/2008 | Luo et al. |

FOREIGN PATENT DOCUMENTS

| | | |
|---|---|---|
| WO | WO-91/08307 | 6/1991 |
| WO | WO-99/09216 | 2/1999 |
| WO | WO-2005/030929 | 4/2005 |

OTHER PUBLICATIONS

International Search Report and Written Opinion for PCT/US2010/031625, mailed Jul. 29, 2010 10 pages.

*Primary Examiner* — Christine T Mui
(74) *Attorney, Agent, or Firm* — Morrison & Foerster LLP

(57) ABSTRACT

Polymeric sequence probes and methods are described that enhance the speed and sensitivity of detection of target analytes by combining a multiplicity of binding moieties specific for analyte, at least two of which are linearly arranged and optionally a multiplicity of detectable labels.

29 Claims, 10 Drawing Sheets

1. Capture probe covalently attached to the surface

2. Target molecule was captured by capture probe

3. Reporter probe was added to report the target molecule

4. Fluorescence complementary reporter was added to report the target molecule as a 1 um fluorescent ball A schematic of ssDNA assay using the special long reporter.

Figure 1. The general concept and structures of polymeric sequence probe.

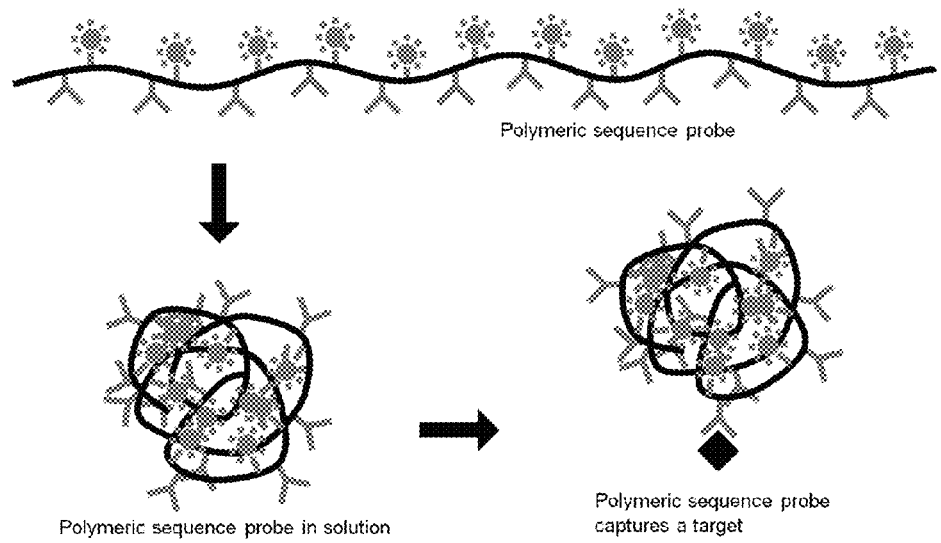
Figure 2.
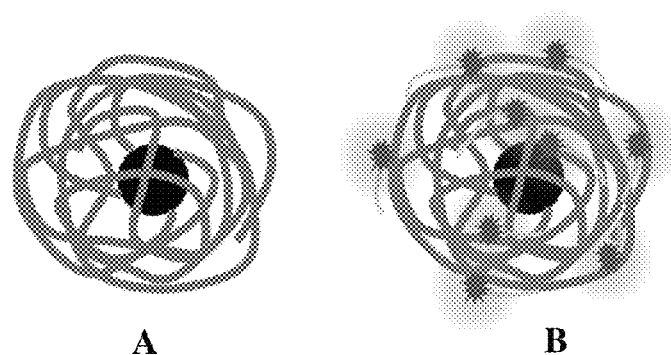
Figure 3. (A) The polymeric sequence probe can be labeled by adding a "core" to it. (B) The polymeric sequence probe with a "core" can be further labeled with other tags.

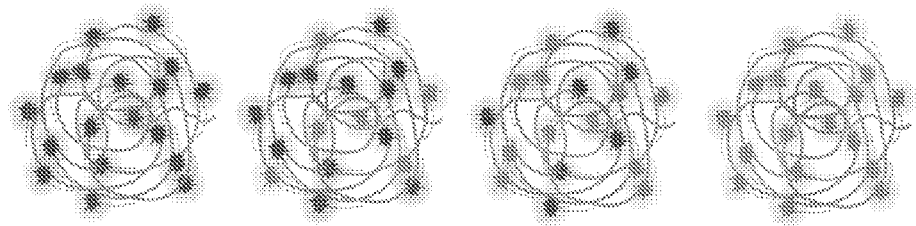
Figure 4. The polymeric sequence probes labeled by two different fluorophores with controlled ratio.
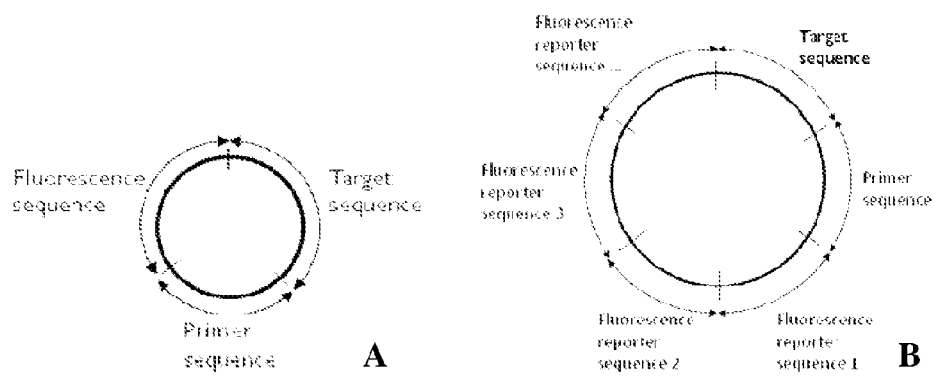
Figure 5. (A) RCA circle template for single color probes. (B) RCA circle template for multiple color probes.

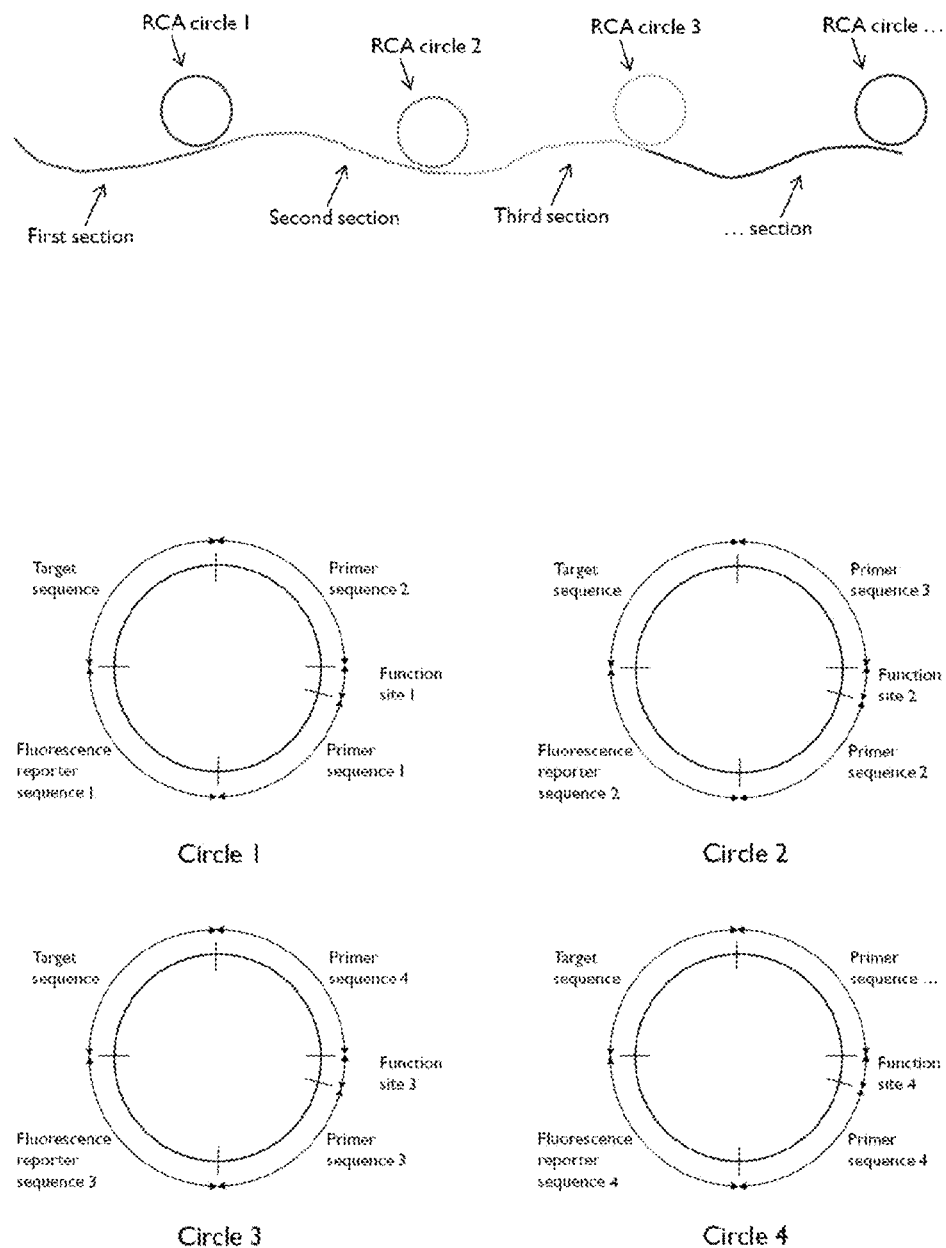
Figure 6. (top) The scheme of making the special probe with more than one circle. (bottom) RCA circle template design for using more than one circle.

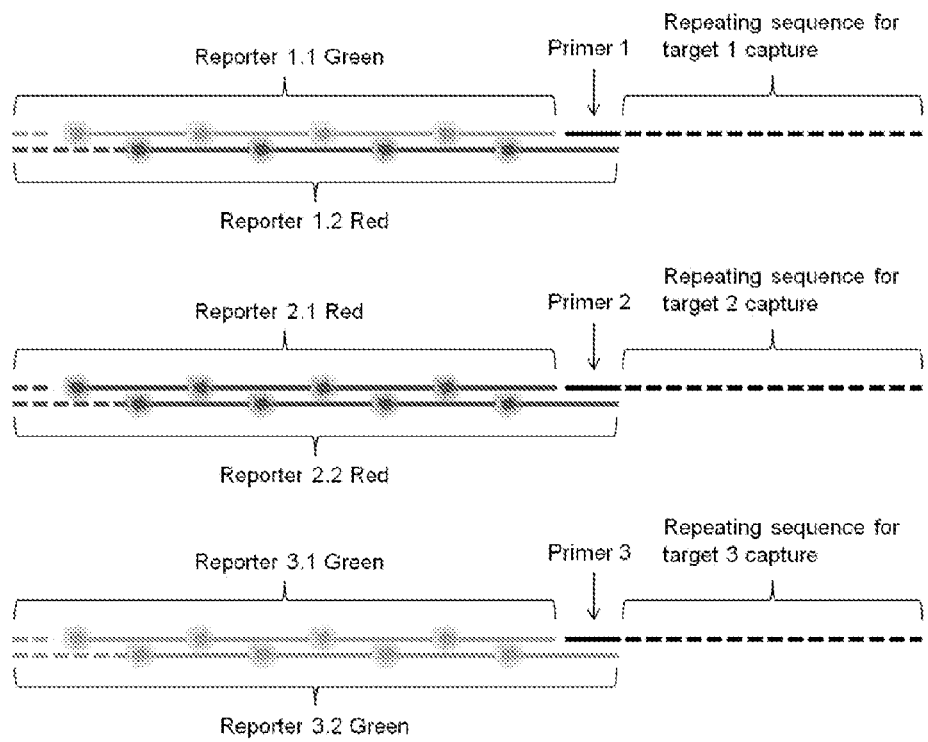
Figure 7. The scheme of making multiplex probes by adding short fluorescent complementary oligos to one end of the probe.
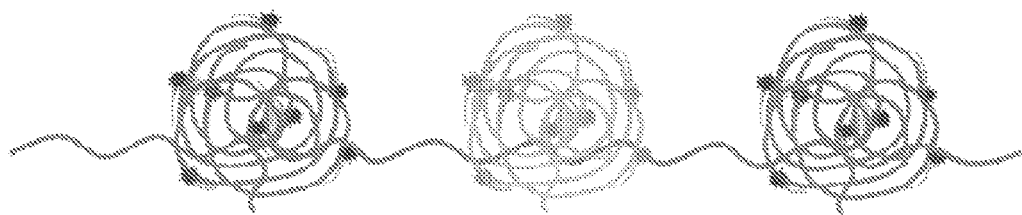
Figure 8. The scheme of multiplex assay performed by adding more special probes to one target molecule.

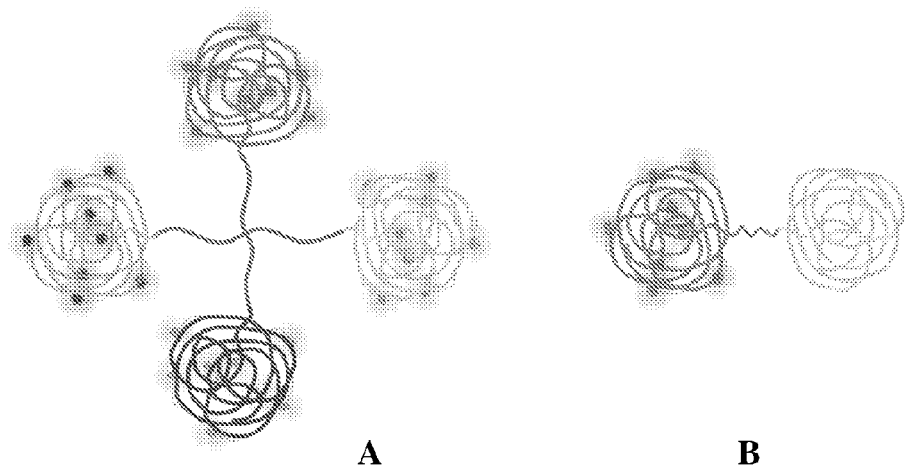

Figure 9. Star structured polymeric sequence probe labeled with different tags. (A) Four-arm star structure. (B) Two-arm star structure/linear structure.

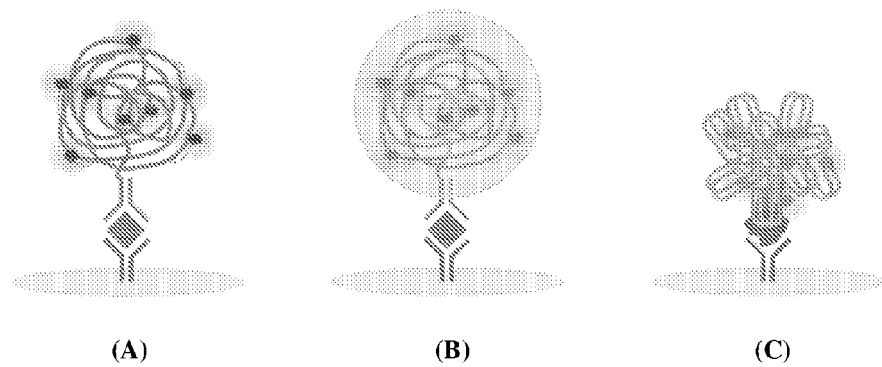

Figure 10. (A) The scheme of labeling proteins with special probes conjugated with antibody. (B) The scheme of protecting the special probe with hydrogel. (C) The scheme of labeling proteins with special probes containing aptamer sequences.

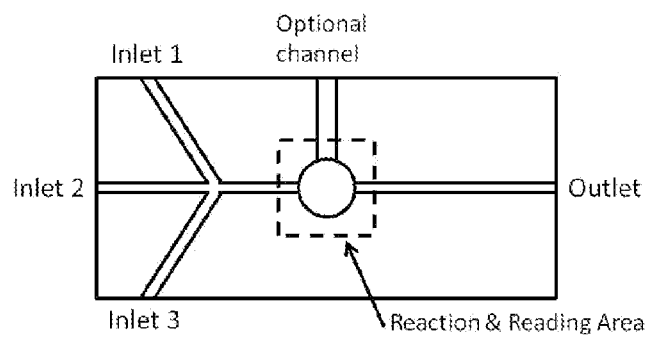
Figure 11A
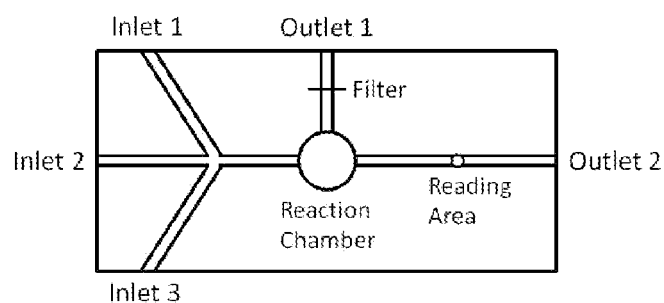
Figure 11B
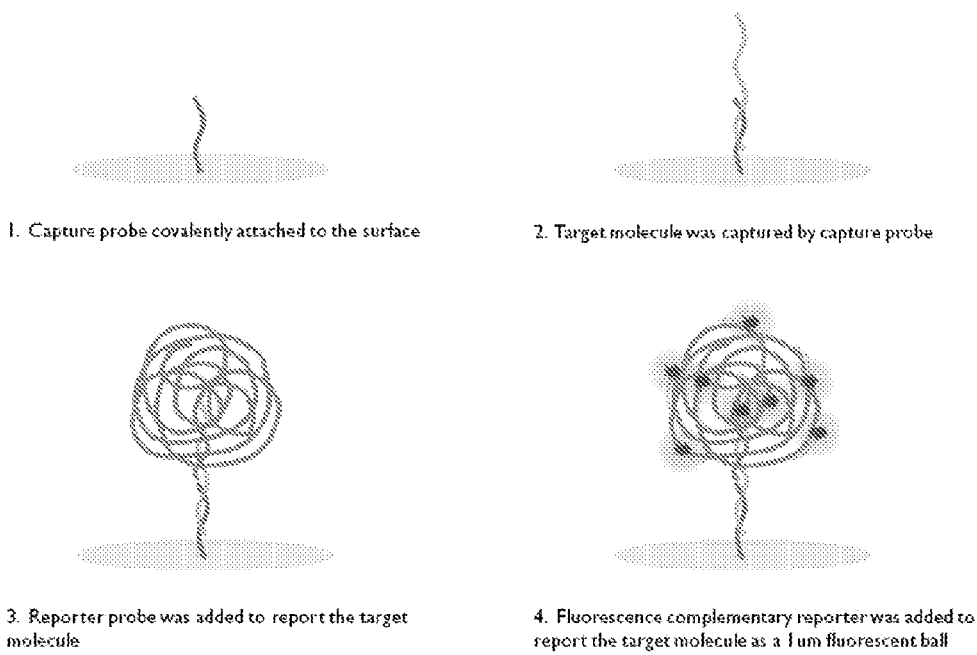
Figure 12. A schematic of ssDNA assay using the special long reporter.

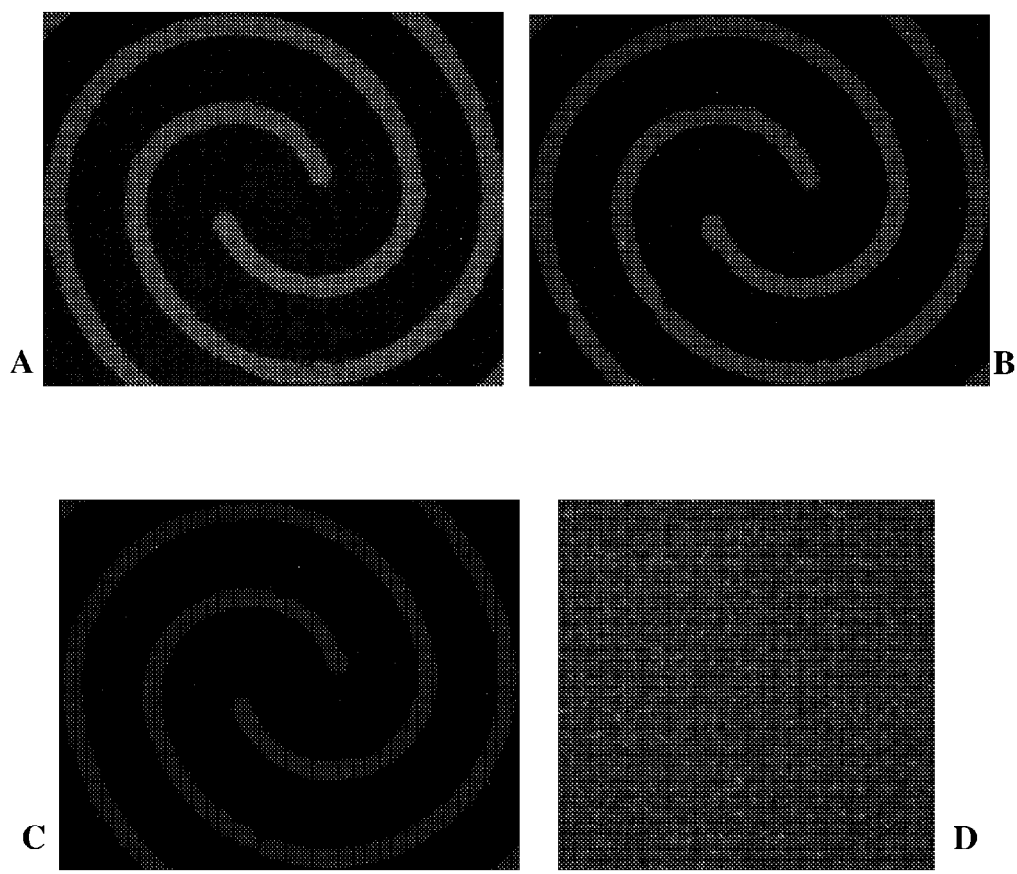
Figure 13. Fluorescence images of captured target molecules ((A) 10 pM, (B) 100 fM, (C) 1 fM, (D) large area 10 pM) labeled by long reporter probes.

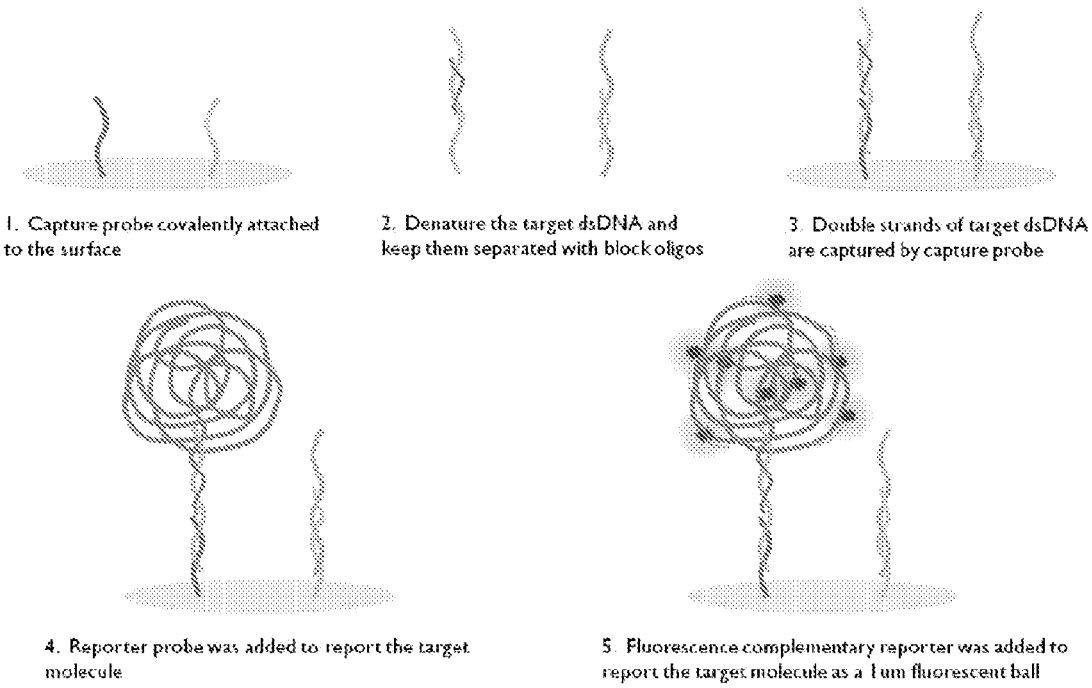
Figure 14. A schematic of dsDNA assay using the special long reporter.
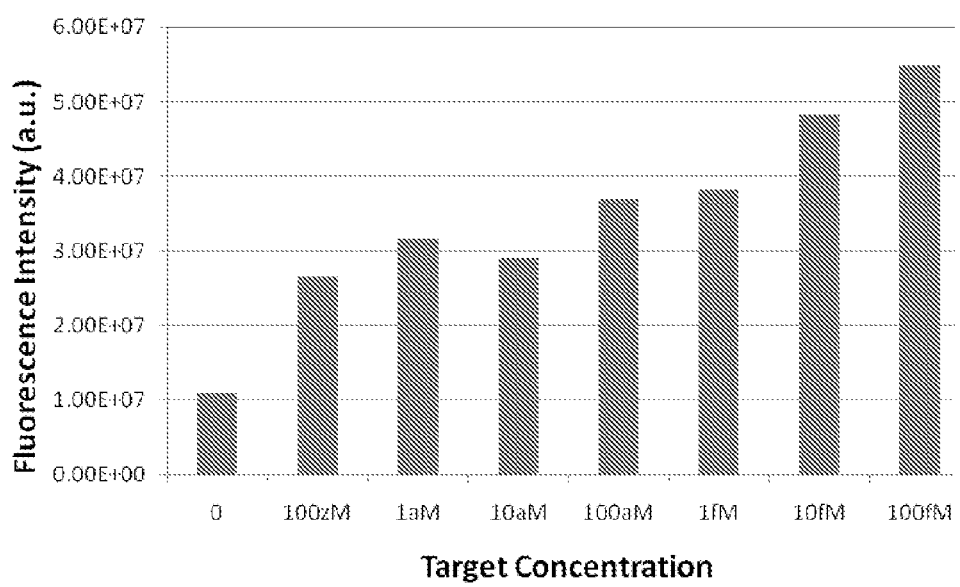
Figure 15. The titration curve shows the fluorescence intensities versus dsDNA target molecule concentrations.

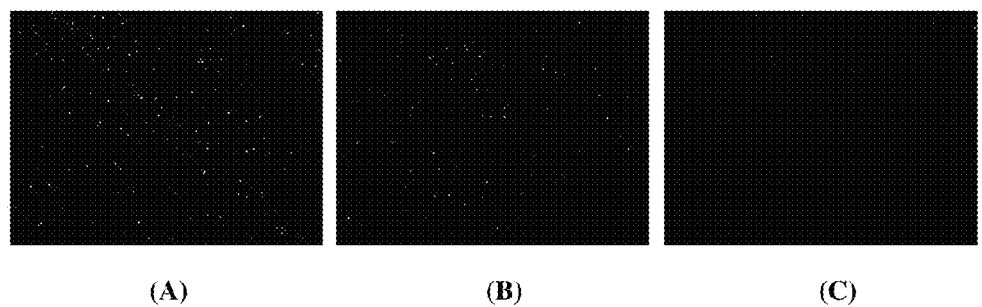
Figure 16. Darkfield images of captured target molecules ((A) 10 fM, (B) 1 fM, (C) negative control) labeled by polymeric sequence probes with Au nanoparticle "core" tags.

```
                        SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: synthetically constructed capture probe
<220> FEATURE:
<221> NAME/KEY: misc_feature
<222> LOCATION: 1
<223> OTHER INFORMATION: n = thiol-C6 modified cytosine

<400> SEQUENCE: 1
ngagtacgcc ttcttgttgg                                                   20

<210> SEQ ID NO 2
<211> LENGTH: 80
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: 1
<223> OTHER INFORMATION: n = phosphate-modified guanine

<400> SEQUENCE: 2
nagcagacaa cgaggacacg tttttttttt tttttttttt tttttatcga gcaagccatc       60
tggacccgtt tttttttttt                                                   80

<210> SEQ ID NO 3
<211> LENGTH: 20
<212> TYPE: DNA
<213> ORGANISM: Artificial Sequence
<220> FEATURE:
<223> OTHER INFORMATION: synthetically constructed fluoro-complement
<220> FEATURE:
<221> NAME/KEY: misc_feature
<222> LOCATION: 1
<223> OTHER INFORMATION: n = cy3-modified guanine

<400> SEQUENCE: 3
nagcagacaa cgaggacacg                                                   20

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
aaaaaaaaaa aaaaaaaaaa aaaaa                                             25

<210> SEQ ID NO 5
<211> LENGTH: 40
<212> TYPE: DNA
<213> ORGANISM: Artificial Sequence
```

```
<220> FEATURE:
<223> OTHER INFORMATION: synthetically constructed target

<400> SEQUENCE: 5
gagcaagcca tctggacccg ccaacaagaa ggcgtactcg                        40

<210> SEQ ID NO 6
<211> LENGTH: 38
<212> TYPE: DNA
<213> ORGANISM: Artificial Sequence
<220> FEATURE:
<223> OTHER INFORMATION: synthetically constructed sense capture probe
<220> FEATURE:
<221> NAME/KEY: misc_feature
<222> LOCATION: 1
<223> OTHER INFORMATION: n = thiol-C6 modified adenine

<400> SEQUENCE: 6
naaaaaaaaa aaaatctcg gctagtgcat tgtcatag                          38

<210> SEQ ID NO 7
<211> LENGTH: 37
<212> TYPE: DNA
<213> ORGANISM: Artificial Sequence
<220> FEATURE:
<223> OTHER INFORMATION: synthetically constructed anti-sense capture
      probe
<220> FEATURE:
<221> NAME/KEY: misc_feature
<222> LOCATION: 1
<223> OTHER INFORMATION: n = thiol-C6 modified adenine

<400> SEQUENCE: 7
naaaaaaaaa aaaagacct gaaagacgtt atccacc                           37

<210> SEQ ID NO 8
<211> LENGTH: 75
<212> TYPE: DNA
<213> ORGANISM: Artificial Sequence
<220> FEATURE:
<223> OTHER INFORMATION: synthetically constructed sense circle
<220> FEATURE:
<221> NAME/KEY: misc_feature
<222> LOCATION: 1
<223> OTHER INFORMATION: n = phosphate-modified thymine

<400> SEQUENCE: 8 nttttttga gcagacattg aggacagctt tttttttttt tttttttttt tttacaagaa   60
ggcgtactcg acctg                                                  75

<210> SEQ ID NO 9
<211> LENGTH: 75
<212> TYPE: DNA
<213> ORGANISM: Artificial Sequence
<220> FEATURE:
<223> OTHER INFORMATION: synthetically constructed anti-sense circle
<220> FEATURE:
<221> NAME/KEY: misc_feature
<222> LOCATION: 1
<223> OTHER INFORMATION: n = phosphate-modified thymine

<400> SEQUENCE: 9
nttttttttt ttttttacga acacacacga ctaccttttt ttttttgatcg tctcggctag  60 tgctttttt ttttt                                                    75

<210> SEQ ID NO 10
<211> LENGTH: 20
<212> TYPE: DNA
```

```
<213> ORGANISM: Artificial Sequence
<220> FEATURE:
<223> OTHER INFORMATION: synthetically constructed sense
      fluoro-complement
<220> FEATURE:
<221> NAME/KEY: misc_feature
<222> LOCATION: 1
<223> OTHER INFORMATION: n = cy3-modified guanine

<400> SEQUENCE: 10
nagcagacat tgaggacagc                                              20

<210> SEQ ID NO 11
<211> LENGTH: 20
<212> TYPE: DNA
<213> ORGANISM: Artificial Sequence
<220> FEATURE:
<223> OTHER INFORMATION: synthetically constructed anti-sense
      fluoro-complement
<220> FEATURE:
<221> NAME/KEY: misc_feature
<222> LOCATION: 1
<223> OTHER INFORMATION: n = 6-FAM modified thymine

<400> SEQUENCE: 11
nacgaacaca cacgactacc                                              20

<210> SEQ ID NO 12
<211> LENGTH: 160
<212> TYPE: DNA
<213> ORGANISM: Artificial Sequence
<220> FEATURE:
<223> OTHER INFORMATION: synthetically constructed sense target

<400> SEQUENCE: 12
acaagaaggc gtactcgacc tgaaagacgt tatccaccat acggataggg gatctcagta    60
cacatcgatc cggttcagcg agcggctcgc cgaggcaggc atccaaccgt cggtcggagc   120
ggtcggaagc tcctatgaca atgcactagc cgagacgatc                         160

<210> SEQ ID NO 13
<211> LENGTH: 160
<212> TYPE: DNA
<213> ORGANISM: Artificial Sequence
<220> FEATURE:
<223> OTHER INFORMATION: synthetically constructed anti-sense target

<400> SEQUENCE: 13
gatcgtctcg gctagtgcat tgtcatagga gcttccgacc gctccgaccg acggttggat    60
gcctgcctcg gcgagccgct cgctgaaccg gatcgatgtg tactgagatc ccctatccgt   120
atggtggata acgtctttca ggtcgagtac gccttcttgt                         160
```

BIOASSAYS BASED ON POLYMERIC SEQUENCE PROBE

RELATED APPLICATION

This application claims benefit of U.S. provisional application Ser. No. 61/293,477 filed 8 Jan. 2010 which is incorporated herein by reference in its entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 655822000400Seqlist.txt | Jun. 29, 2010 | 4,052 bytes |

TECHNICAL FIELD

The invention relates to bioassays based on polymeric probes for analyte recognition. More particularly, the invention is based on a polymeric probe with repeated regions comprising binding partners for an analyte, especially biomolecules, and repeated labeling regions.

BACKGROUND ART

Various assays have been developed to recognize target analytes based on biomolecular probes. The biomolecular probes generally include a capture portion, e.g., nucleic acids or peptides that can selectively bind with targeted biomolecules or biological systems such as cells, tissues and organs. The sensitivities of these bioassays are limited by the binding affinity between the probes and target molecules based on various factors, such as kinetic reaction rate, conjugation chemistry, and steric hindrance, especially when the concentrations of target molecules are low. Currently many biomolecular assays rely on target molecule amplification techniques such as polymerase chain reaction (PCR), which add extra cost and complexity, and limit the speed of the assay. Present biomolecular probes generally also include reporters such as fluorophores, metal nanoparticles, fluorophore clusters, fluorophore-conjugated antibodies/proteins, fluorophore encapsulated nanoparticles, quantum dots and enzymes. Among these reporter probes, solid-core nanoparticle probes, such as fluorophore encapsulated nanoparticles, quantum dots, and metal nanoparticles have high surface-volume ratio, tend to precipitate, aggregate, and nonspecifically bind to the surface or to other biomolecules. The non-specific binding gives false signals and leads to high noise, limiting the sensitivity, specificity, and dynamic range of the biomolecular assay. Nanoparticle probes are also sensitive to their concentration in the solution, the pH value and the ion concentration. On the other hand, the molecule based reporter probes, such as fluorophores, fluorophore clusters, fluorophore conjugated antibodies, or proteins do not provide strong signals for ultra sensitive biomolecular detection. Enzymes are used extensively in ELISA (Enzyme-linked immunosorbent assay) for signal amplification in antibody-antigen detection. However, because of the non-specific binding, non-specific amplification, and high background noises, the assay cannot reach ultra-high sensitivity, and its dynamic range is usually less than three orders of magnitude.

Attempts have been made to overcome these disadvantages in the past, but generally fall short. For example, U.S. Pat. No. 5,175,270 describes dendritic forms of nucleic acids that offer multiple regions of complementarity to target. U.S. Pat. No. 5,635,352 provides a complicated system of capture probes, capture extenders, label probes and label extenders to multiply the effects specifically on detection of nucleic acids. US2006/0286583 describes multiplexed branched chain DNA assays for detecting two or more nucleic acids. PCT publication WO91/08307 describes enhanced capture of target nucleic acids by the use of oligonucleotides covalently attached to polymers; however, the capture polynucleotides are at the ends of branches of the polymer as opposed to linearly aligned. US2008/0038725 illustrates the use of rolling circle amplification to provide binding sites for a multiplicity of labels after target analytes have been captured. It needs long amplification time after the target analytes have been captured. Moreover, none of these documents suggests combining on the same macromolecular backbone, a multiplicity of binding partners or recognition sites with at least two such sites arranged linearly.

The present invention provides reagents and assays that have advantages over known methods of analyte detection, including high specific binding/capture rate, strong reporting signals, low nonspecific binding rate, and high stability.

DISCLOSURE OF THE INVENTION

By providing on a single polymeric sequence probe a multiplicity of capture regions designed to interact specifically with a target analyte, and optionally a multiplicity of either reporter labels or capture regions for reporter labels, the polymeric sequence probe of the invention overcomes the obstacles encountered previously in the art. It is unnecessary to amplify the target analyte since the capture reagent is already amplified and signal is enhanced by the multiplicity of labels. The target analyte can be detected either in solution or on a support such as a chip or bead surface.

Thus, in one aspect, the invention is directed to a polymeric sequence probe for detection of target analyte which polymeric sequence probe comprises a macromolecular backbone, along which is disposed a multiplicity of recognition sites specific for said target analyte. At least two recognition sites must be arranged linearly. In some embodiments at least 3, 5, 10, 50 or more recognition sites are arranged linearly.

These polymeric sequence probes optionally further contains either:

(a) a multiplicity of detectable label sites; or
(b) a multiplicity of detectable labels; or
(c) a labeling microparticle or nanoparticle coupled to said macromolecular backbone, or
(d) any combination thereof. Thus the probe may include both (a) and (c) or both (b) and (c), or both (a) and (b) or all of (a), (b) and (c).

These polymeric sequence probes may also contain, disposed along said backbone, a second multiplicity of recognition sites specific for a second, different target analyte, and optionally, a first and second multiplicity of label sites or labels wherein said first and second label sites or labels are different. Third recognition sites and label sites may also be included, and higher numbers are also within the scope of the invention.

In another embodiment, the invention includes a polymeric sequence probe for detection of a target analyte which polymeric sequence probe comprises a macromolecular backbone, along which is disposed at least a first and second multiplicity of label sites or labels wherein said first and second label sites or labels are different, and optionally at least one recognition site. Third and fourth or more label sites may also be included.

The backbone may either be linear, branched, circular, dendritic or combinations thereof.

The recognition sites may either be integral to the macromolecular backbone or may be appended thereto. For example, if the macromolecular backbone is a nucleic acid, the recognition site may be an aptamer designed to recognize a target or a nucleotide sequence complementary to a nucleic acid target. If the macromolecular backbone is a poly-peptide, the recognition site may be a peptide or an epitope. Alternatively, the recognition sites or label sites may be antibodies or antibody fragments coupled to the macromolecular backbone. "Label sites" are portions of the backbone to which a detectable label can be bound.

Similarly, the detectable label sites may be a part of the backbone or may be appended thereto. The polymer itself may constitute a detectable label as further described below or labels may be coupled to portions of the macromolecular backbone through various linkages, covalent and non-covalent.

In another aspect, the invention is directed to a method to make an exemplary polymeric sequence probe comprising nucleic acid or comprising a peptide in an efficient and economic way.

In another aspect, the invention is directed to a method to detect target analyte using the polymeric sequence probes of the invention and to kits for carrying out the method.

In still another aspect, the invention is directed to a multi-labeled reagent which comprises two or more same or different labels which reagent is a partially double-stranded nucleic acid wherein each strand of the double-stranded portion is labeled with each same or different label, and wherein the single-stranded portion is complementary to a target analyte.

Because of the efficiency of detection, the reaction speed is greatly enhanced and thus the time required for the assay is reduced. Enhanced sensitivity is also exhibited by use of the methods of the invention.

BRIEF DESCRIPTION OF DRAWINGS

FIG. 2 shows one example of the polymeric sequence probes of the invention. In this example, the recognition sites comprise antibodies and the probe includes multiple fluorescence labels. The figure also shows the formation of a "ball" by the linear probe and its binding to antigen.

FIG. 3 shows two forms of a polymeric sequence probe that contains a core. In FIG. 3A, the core particle is the only label; in FIG. 3B, additional label is distributed over the polymeric backbone.

FIG. 4 shows, schematically, polymeric sequence probes that are labeled by two different fluorophores with different ratios.

FIG. 5A shows a rolling circle amplification (RCA) circle template for single label probes. FIG. 5B shows an RCA circle template for multiple label probes.

FIG. 6 shows the scheme of making a polymeric sequence probe with more than one circle. Four different RCA circle template designs for use in this method are shown at the bottom.

FIG. 7 shows a multiplexed reagent wherein short fluorescent complementary oligos are coupled to one end of an oligo. These may be used as labels in the polymeric sequence probe.

FIG. 8 shows a multiplex assay performed by adding several probes to one target molecule.

FIGS. 9A and 9B show particular embodiments of the probes of the invention.

FIG. 10A shows embodiments wherein proteins/antigens are labeled with probe conjugated with antibody. FIG. 10B shows protection of the probe with hydrogel. FIG. 10C shows labeling of protein with aptamer-based recognition sites on the probe.

FIGS. 11A and 11B show, diagrammatically, microfluidic/nanofluidic devices that can be used to conduct the assays on surfaces or in solution, respectively.

FIG. 12 shows a schematic of ssDNA assay using the invention probe.

FIG. 13 shows fluorescence images of captured target molecules (A: 10 pM, B: 100 fM, C: 1 fM, D: large area 10 pM) labeled by the invention probe.

FIG. 14 shows a schematic of dsDNA assay using the invention probe.

FIG. 15 is a titration curve of fluorescence intensities versus dsDNA target molecule concentrations.

FIG. 16A-C show images of captured target molecules labeled with the invention probe containing a gold nanoparticle core tag. FIG. 16A shows the results when the target is at 10 fM; FIG. 16B shows the results when the target is at 1 fM and the negative control is shown as 16C.

MODES OF CARRYING OUT THE INVENTION

Figure 1:
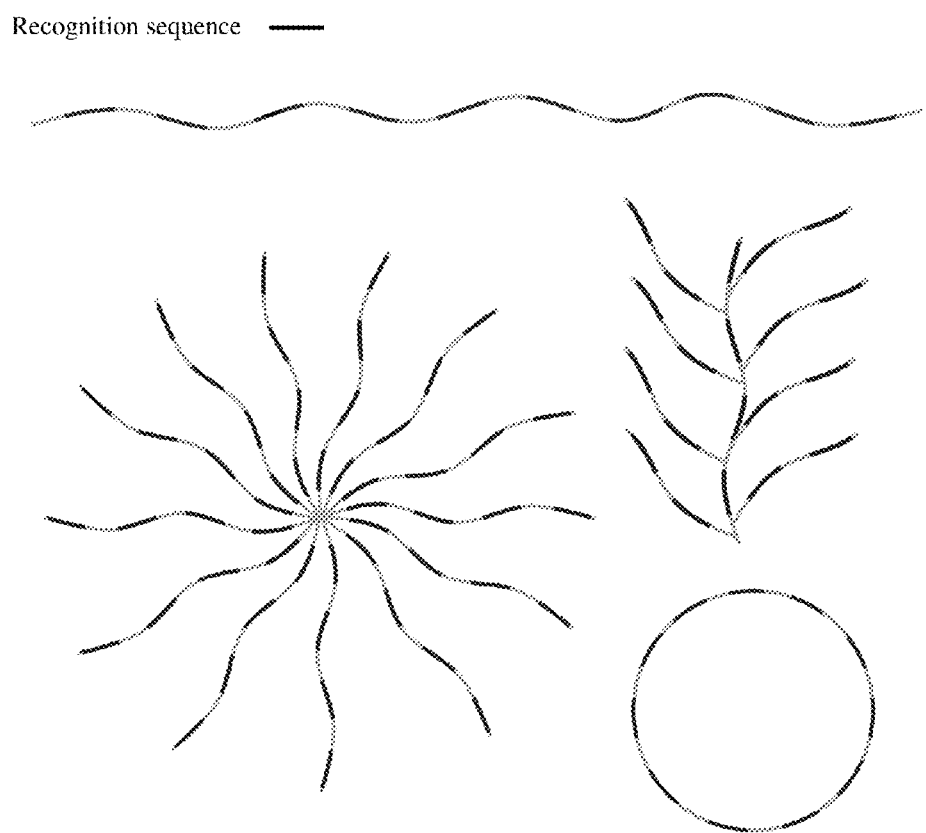
FIG. 1 shows diagrammatically the general concept and structures of polymeric sequence probes.

Unless defined otherwise, technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a", "an" and "the" include plural referents unless the context clearly dictates otherwise.

The present invention provides bioassays based on a polymeric sequence probes. The invention includes the polymeric sequence probes themselves as well as methods to make and use them.

The polymeric sequence probes of the invention are polymers with repeated regions, i.e., "recognition sites" able specifically to bind an analyte. These recognition sites may be nucleotide sequences, amino acid sequences, including binding portions of antibodies, receptors, ligands and the like, or combinations thereof. The recognition sites may be an integral part of the probe backbone or may be appended thereto by suitable linkages. Thus, the "polymeric sequence probe" of the invention is a polymer with repeating sequences or adjuncts that behave as selective binding sites or recognition sites for target analytes.

The polymer may be a synthesized polymer or a natural biopolymer such as nucleic acid or protein. The backbone polymer can be linear, branched, circular, dendritic, including a star structure, or may be a combination. (See FIG. 1.) Nevertheless, as shown, the backbone polymer must contain at least two, preferably three or more, and more preferably 10 or more recognition sites that are in a linear relationship with each other. In a dendritic structure, each arm can be a linear structure, a branch structure including brush or comb structures, or combinations thereof; in a branch structure, each branch can be a linear structure, a dendritic structure, or combinations thereof. The multi-binding polymeric probe contains a multiplicity of the same recognition site or a multiplicity of each of two or more different recognition sites. The recognition sites of the polymer selectively bind target analytes such as nucleic acids, proteins, antibodies, antigens with high binding rates, high selectivity, high sensitivity, and high specificity. Since the polymeric sequence probes of the invention have a multiplicity of recognition sites for each target, the concentration of the recognition sites is effectively increased. Thus, in the methods of the invention, rather than amplifying the target to increase its concentration, the sensitivity of the assay is improved by raising the concentration of the recognition sites. This effectively raises the concentration of the detection reagent.

The recognition sites in the polymeric sequence probe are repeated over a range of $10$-$10^5$ or intermediate numbers of recognition sites may also be present, and all intervening numbers are included, including $10^2$, $10^3$ and $10^4$ recognition sites.

Both the sensitivity of the assay, and the speed of the assay are greatly improved. Assays using the probes of the invention are able to detect single molecules or concentrations of single molecules in one milliliter.

The reaction time between the probe and targeted molecules ranges from 1 second to 10 hours and all intervening units of time, such as 1 minute, 10 minutes, 1 hour, 5 hours or 6 hours.

The polymeric sequence probe also exhibits very low non-specific binding rates with non-targeted molecules, species or environments in the assays. The ratio between the specific binding rates with the targets to the nonspecific binding rates with non-targeted molecules, species or environments may be as high as $10^{15}$ and intervening ratios such as 10, $10^2$, $10^4$, $10^6$, $10^{10}$ and $10^{12}$.

While not intending to be bound by any theory, the high ratio of binding to target as compared to non-targeted molecules or surfaces may be due to the plethora of recognition sites and lack of portions that bind non-specifically, as well as to solubility of many of the polymeric sequence probes thus minimizing their interaction with surfaces. In some instances, electrical forces between the probes and non-target molecules or surfaces may be taken advantage of.

In one embodiment, the polymeric sequence probe is composed of a nucleic acid with repeated binding nucleotide sequences such as DNA (deoxyribonucleic acid), PNA (peptide nucleic acid), RNA (ribonucleic acid), Morpholino, locked nucleic acid (LNA), glycol nucleic acid (GNA), threose nucleic acid (TNA), or combinations thereof.

Alternatively, polymeric sequence probe is composed of peptides or proteins with repeated sequences of amino acids, including antibodies. The peptides or proteins may also be modified to have modified peptide linkages such as $CH_2N$ and the like.

In some embodiments, the polymeric sequence probes are combination of nucleic acids and proteins. These probes may also include portions which constitute alternative oligomers or polymers formed as, for example, polystyrene, polyacrylates, polycarbonates, polyesters, polyamides and the like. These portions may contain reactive groups, such as amino groups, sulfhydryl groups, carboxyl groups, amino groups, for example, which, if desired, may be employed to couple binding agents for providing the recognition sites such as antibodies or ligands or receptors.

Methods for conjugation of binding reagents and labels to macromolecular backbones are generally known in the art. For example, in one method, an amide linkage is formed between an amino group and a carboxylic acid group; thus, a binding reagent or label comprising an amino group can be conjugated to a backbone comprising a carboxylic acid group, or a binding reagent or label comprising a carboxylic acid group can be conjugated to a backbone comprising an amino group. The conjugation may be performed by reacting the binding reagent or label and backbone in the presence of a condensing agent, for example a carbodiimide such as dicyclohexylcarbodiimide (DCC) or 1-(3-dimethylaminopropyl)-3-ethylcarbodiimide (EDCI), a uronium reagent such as O-benzotriazole-N,N,N',N'-tetramethyluronium-hexafluorophosphate (HBTU), or a phosphonium reagent such as benzotriazole-1-yl-oxy-tris-(dimethylamino)phosphonium hexafluorophosphate (BOP).

Alternately, the carboxylic acid group may be activated for conjugation in a prior step, for example by conversion to an acid chloride using thionyl chloride or oxalyl chloride, or to an active ester such as a pentafluorophenyl ester using a carbodiimide and pentafluorophenol or an N-hydroxysuccinimidyl ester using a carbodiimide and N-hydroxysuccinimide, and the resulting activated carboxylate may then be reacted with the amine in a second step. The amine and carboxylic acid groups may initially be present in protected form as required for stability and/or compatibility with additional chemical transformations, and deprotected prior to the conjugation step. Amine groups may be protected as carbamates, preferably tert-butoxycarbonyl ($^t$BOC), allyloxycarbonyl (Alloc), or other carbamate groups that may be removed under neutral-to-acidic conditions. Carboxylic acids may be protected as esters that may be removed under neutral-to-acidic conditions, such as tert-butyl ($^t$Bu), trityl ($Ph_3C$), allyl (All), or methoxymethyl (MOM).

In another method, a thioether linkage is formed between a thiol group and a maleimide group; thus, a binding reagent or label comprising thiol group can be conjugated to a backbone comprising a maleimide group, or a binding reagent or label comprising a maleimide group can be conjugated to a backbone comprising a thiol group. The thiol group may initially be present in protected form as required for stability and/or compatibility with additional chemical transformations, and deprotected prior to the conjugation step. Suitable protecting groups include those that may be removed under neutral-to-acidic conditions, for example tert-butyl ethers ($^t$Bu) or trityl ethers.

In still another method, a 1,2,3-triazole linkage is formed between an alkyne and an azide group; thus, a binding reagent or label comprising an alkyne group can be conjugated to a backbone comprising an azide group, or a binding reagent or label comprising an azide group can be conjugated to a backbone comprising an alkyne group. The conjugation reactions may be performed under metal catalysis, typically using copper or ruthenium, or may be performed in the absence of catalyst using an activated alkyne such as a cyclo-octyne.

In another method, an enamino-ketone linkage is formed between an amino group and a 1,3-dicarbonyl group; thus, a binding reagent or label comprising an amino group can be conjugated to a backbone comprising a 1,3-dicarbonyl group, or a binding reagent or label comprising a 1,3-dicarbonyl group can be conjugated to a backbone comprising an amine group. In one embodiment, a binding reagent or label comprising a 1,3-dicarbonyl group is reacted with an antibody such as m38C2 comprising a suitably reactive lysine e-amino group (Doppalapudi, et al., *Bioorganic & Medicinal Chemistry Letters* (2007) 17:501-506, incorporated herein by reference).

Typical targets or target analytes for detection are biomolecules. A "biomolecule" is any organic molecule that is produced by a living organism, including large polymeric molecules such as proteins, polysaccharides, and nucleic acids as well as small molecules such as primary metabolites, secondary metabolites, and natural products.

The "target", "targets", "target analyte" or "target analytes" to be detected by the invention probe may be biomolecules or other entities. Targets or target analytes can include, for example, pharmaceutical species; biomacromolecules such as, proteins and antibodies (monoclonal or polyclonal), DNA, and RNA, expressed by bacterial, mammalian, plant, or insect cells; enzymes; tissues, minerals; and manmade chemical species such as, for example, synthetic small organic molecules, peptides and polypeptides, oligosaccharides, and sugar modified proteins. In some embodiments, the target molecule may be one or more impurities or waste products, including proteins; inorganic species such as metals, metal ions, or ions such as carbonates, sulfates, oxides, phosphates, bicarbonates, and other ions commonly found in industrial, residential and biological feed streams; small organic molecules such as those that comprise dyes, pesticides, fertilizers, additives, and stabilizers; process byproducts and pollutants; DNA, RNA, phospholipids, viruses, or other cell debris from a bioprocess.

The term "target" or "target analyte" may also include a portion of the molecule to be detected. Thus, the target analyte may be a single epitope on a protein or a single subsequence on a nucleic acid. Thus, first and second target analytes may reside on the same biomolecule. While different recognition sites on the same polymeric sequence probe can be used to determine separate epitopes or separate subsequences on the same biomolecule, more typically for such determinations, multiple polymeric sequence probes having different recognition sites may be used.

The terms "peptide", "polypeptide" and "protein" are used interchangeably regardless of the length of the amino acid sequence.

"Capture probe" refers to a "probe" which is used to capture target, often to bind the target to a solid substrate.

"Complementary" refers to a nucleotide sequence that binds to another nucleotide sequence by hybridization. Some mismatches, e.g., 0-30% mismatches, may be tolerated.

The term "oligo" is used for short, single-stranded nucleic acid fragments, such as DNA or RNA, or similar fragments of analogs of nucleic acids such as PNA or morpholinos.

A "multiplex assay" is a type of laboratory procedure that simultaneously measures multiple targets (two or more) in a single assay.

Labels

In addition to the multiplicity of recognition sites contained on the macromolecular backbone of the polymeric sequence probe, the probe may also contain either detectable labels or binding sites for detectable labels. This is shown, for example, in FIG. 2 where the polymeric sequence probe contains antibodies as recognition sites for the target and fluorescent molecules as detectable label.

The coupling of labels to the polymeric sequence probe is effected in a manner dependent on the nature of the probe. For example, if the polymeric sequence probe is a nucleic acid, regions are provided that recognize oligomers attached to detectable labels which thus secure the detectable labels to the probe. In some instances, the oligomer itself may constitute a label if detection is by sensors that can register such complexation. Both nucleic acid-based probes and protein-based probes may be labeled by using linkers to react with sidechain functional groups, such as SH, $NH_2$, hydroxyl or carboxylic acids, or these groups in synthetic polymers may be used to couple the labels as described above. Alternatively, the label may be coupled non-covalently by interaction of, for example, label coupled to a ligand to a receptor sequence contained in the polymeric sequence probe. In some cases, dyes such as SYBR® green, SYBR® gold, or ethidium bromide may bind directly to regions of the polymeric sequence probe that are uncomplexed with target.

In one embodiment, a single label may be employed as a "core" to which the polymeric sequence probe is bound. Suitable cores are detectable particles such as gold particles which may be sufficient to label the probe without the necessity for additional label spaced along the polymeric sequence probe as shown in FIG. 3A or the probe may contain additional label as shown in FIG. 3B. The "core" may be a microparticle (i.e., diameter measured in μ) or a nanoparticle (i.e., a diameter measured in nm). Microparticles include microspheres, microbeads and any particles measured on a micro scale regardless of shape. Nanoparticles include nanospheres, nanocrystals, nanorodes, nanburgers, and the like, i.e., any particles measured on a nanoscale regardless of shape, and quantum dots.

The polymeric sequence probes can be detected through various methods including but not limited to optical, electrochemical, electrical, magnetic, chemical, biochemical, piezoelectric methods, and combinations thereof.

One of the major advantages that the polymeric sequence probe provides for the assay is that it can be made to the sizes such that the presence of a single target can be detected directly by an optical microscope. In addition, optical sensors can detect the changes of absorbance, scattering, or reflection optical signals caused by the invention probes.

The polymeric sequence probe can be detectable by piezoelectric sensors. Piezoelectric sensors utilize crystals that undergo an elastic deformation when an electrical potential is applied to them. An alternating potential (A.C.) produces a standing wave in the crystal at a characteristic frequency. This frequency is highly dependent on the mass bound to the crystal. When polymeric sequence probes and targeted molecules are bound to the crystal, the piezoelectric sensors will produce a change in the resonance frequency, which gives detectable signals of the targeted molecules.

Labels include optical tags, such as organic fluorescence dyes (e.g., fluorescein), inorganic fluorescence dyes (e.g., quantum dots), radioactive isotopes, nanoparticles (metal, glass, magnetic, polymer, etc.), nanocrystals, enzymes, electrochemical tags, electrical tags, and the like, or combinations thereof.

Organic fluorescence dyes include fluorophores such as FITC, FAM, TRITC, DAPI, Alexa Fluor®-series, BODIPY series, Cy series, etc. Nanoparticles or microparticles may compose metal, semiconductor, insulative, organic particles, polymer particles or the combination thereof. The particles can change and enhance the absorbance, scattering, or reflection optical signals from the probe and generate optical signals above background noises. Other labels include magnetic materials such as magnetic particles, organic magnetic materials, magnetic polymers or combinations thereof.

Labels also include electrically charged materials that can be detected by electrical charge sensors such as field effect transistors by generating signals above background noises. These materials include nucleic acids, peptides, proteins, small molecules, monomers, polymers, metals, semiconductors, insulators, or combinations at nanoscale or microscale. Thus, the polymeric sequence probes can function as reporter probes without labeling.

For example, some types of polymeric sequence probes have strong absorption at certain wavelengths, such as nucleic acids which have an absorption peak at 260 nm. Protein polymeric sequence probes have absorption peaks at 280 nm. These types of probes can be detected by optical sensors.

The labels may also be enzymes or other catalytic materials that effect production or consumption of electrons, can be detected by the electrochemical sensors by generating electrical current or potential signals above background noise.

The polymeric sequence probe can thus be designed and engineered with different signal combinations for bioassays, in which signals can be optical signal, electrochemical, electrical, magnetic, chemical, biochemical, piezoelectric signals, etc.

Of course, it is not necessary that the recognition sites in the polymeric sequence probe be identical or designed to bind to a single target. Multiplex assays may be designed by providing recognition sites for more than one target. More typically, however multiplex assays may be designed by providing multiple different polymeric sequence probes with different recognition sites and different label sites, labels or combinations thereof. Further, the specificity of the assay may be enhanced by providing recognition sites for more than one site on a target. For example, recognition sites provided by antibody sequence regions may be provided for two or three epitopes on the same target. This greatly reduces background noise. More typically, the specificity of the assay may be enhanced by providing more than one different polymeric sequence probes with different recognition sites and different label sites, labels or combinations thereof for one target. For example, a protein, such as an antibody or antigen can be recognized by two different polymeric sequence probes at different site on the protein. The two polymeric sequence probes have different label signals. This greatly reduces the false positive rate and background noise.

In addition, controlled ratios of different labels can be included on the same polymeric sequence probe as shown in FIG. 4.

One of the advantages that the polymeric sequence probes can provide is that the detected signals from multiple probes bound with one target can give specific combinations of the signals from the bound probes with the different labels. The specific combinations of the signals may include the combinations of intensities, types, colors, ratios, locations, and temporal related signals. The specific combinations of the signals can eliminate the false signals induced by a non-specifically bound single label.

Synthesis of the Polymeric Sequence Probes

Polymeric sequence probes are made by assistance of enzymes, chemical synthesis, bioconjugations, chemical conjugations, cell culture, or combinations.

In general, methods for synthesizing proteins and nucleic acids and their analogs are well known in the art, as well as are methods for assembling polymers. To prepare polymeric sequence probes that are nucleic acids or their analogs, it is particularly advantageous to employ rolling circle amplification (RCA) where the number of the repeated sequences in a linear nucleic acid polymeric sequence probe can range between 2 and $10^8$, typically 100-$10^3$.

RCA is an isothermal in vitro method for enzymatic synthesis of long DNA with repeating sequences. It is based on the rolling replication of short, single stranded DNA circles by polymerase at constant temperature. This reaction is initiated by the hybridization of a linear ssDNA primer to a specific DNA circle, and then the elongation of the primer by repeating the circle sequence. The long DNA will fold to a soft "ball" in solution.

To make the simplest form of the polymeric sequence probe of the invention which is a nucleic acid molecule containing multiple recognition sites, the circular template will contain the complement to the recognition site as well as a primer recognizing sequence. If the primer is itself complementary to the sequence in the template that is complementary to the recognition site or label site, a separate primer recognizing site is unnecessary. Thus, the template will contain the complement to the intended recognition site and optionally a separate recognizing site for the primer to start the RCA. More complex forms of the polymeric sequence probe of the same type of nucleic acid backbone may be formed by using templates with complements for more than one recognition site; two types of recognition sites may be provided on a single circular template or may be disposed on two or more circular templates.

Polymeric sequence probes having nucleic acid backbones that contain two or more different label sites may be made in a similar way—i.e., using the complement to each of the different label sites either on the same circular template or on multiple circular templates. As in the case of the synthesis of multiple recognition sites or label sites by using more than one circular template, an optionally separate primer recognizing site may also be provided on the template.

For example, to make a linear ssDNA polymeric sequence probe with recognition sites and label-binding sequences, the circle used to make it contains three main sequences: the complement to the recognition site, primer sequence and label sequence where, e.g., a fluorescent label is contained in the same "label" sequence. (FIG. 5A). To ensure the binding affinity of the hybridization, each sequence is usually longer than 12 nucleotides, typically about 18 nucleotides or longer. Some spacer sequences may be applied between two sequences to avoid steric hindrance. The probe made with the circle will contain repeated complementary sequences for all three sequences.

As shown in FIG. 5B, more complex polymer sequence probes may be synthesized in a similar manner by providing circular template with multiple recognition and/or label-associated sequences. In this illustration, sequences for binding three types of label are included in the template.

High levels of complexity are provided by using more complex circular templates and/or using multiple circular templates. As shown in FIG. 6, a very complex polymeric sequence probe is generated by synthesizing a first section with a first circular template that incorporates two different primers and continuing the synthesis with additional circular templates having overlapping primers and multiple recognition and reporter sequences.

As shown in FIG. 6, the reaction can be started with the first type of circle (RCA circle 1) only, using the same protocol as the conventional single step RCA. When the first amplification step finishes, the annealing site, where the circle binds to the probe, is cleaved by a specific enzyme. The first section of the probe is obtained. The first section is the repeating complementary sequence of circle 1. After a denaturing and purification process, the second type of circle (RCA circle 2) is added to the reaction. RCA circle 2 will bind to the 3' end of the probe, and continue elongating the probe using the circle 2 as template. The second section is the repeating complementary sequence of the circle 2. Using the same method, the third section, or even more sections can be added to the probe. Each section can contain a different fluorescence reporter binding site. Therefore, the probe can be tagged with two or more different fluorophores for multiplex applications. Under this strategy, the circle usually contains the target sequence, a unique fluorescence reporter sequence, two primer sequences, and a function site (usually an enzyme restriction site). The first primer sequence is used to start the amplification using this circle. The second primer sequence is for the next circle to bind to the probe. The function site is used to cleave the probe at specific site so the next RCA process can be designed because RCA can only happen at the 3' end of DNA.

The RCA product can be further amplified by *E. coli* or yeast culture or amplified by Polymerase Chain Reaction (PCR) to produce large amounts of probes with low cost. Other linear nucleic acid polymeric sequence probes, such as RNA polymeric sequence probes, can be made by reverse transcription from DNA probes. DNA polymeric sequence probes can also be used to transcript other nucleic acid polymeric sequence probes such as peptide nucleic acid (PNA), locked nucleic acid (LNA), glycol nucleic acid (GNA), threose nucleic acid (TNA), or combinations by the methods for the nucleic acid synthesis described above.

Conversely, other nucleic acid polymeric sequence probes such as peptide nucleic acid (PNA), ribonucleic acid (RNA), locked nucleic acid (LNA), glycol nucleic acid (GNA), threose nucleic acid (TNA), or combinations of them can reversely transcript DNA polymeric sequence probes.

Peptide polymeric sequence probes can be made by translation from nucleic acids or chemical synthesis. Thus, the invention provides an efficient method to prepare peptide-based polymeric sequence probes by taking advantage of the methods to synthesize nucleic acids of any complexity as described above, and then translating the nucleic acid molecule that results into a peptide/protein probe. Translation make be conducted either in vivo or in vitro.

For in vivo translation, the nucleic acid molecule prepared according to the foregoing method is provided with expression control sequences and inserted into host cells for expression and translation into protein. The polypeptide chains thus produced can be extracted from the cells and purified using conventional techniques; purification is eased by the repetitive amino acid sequences included in the resulting polymeric sequence probe. In vitro translation systems are also available as cell-free extracts, for example, from rabbit reticulocytes, wheat germ, *E. coli* and other cellular sources. These systems contain the necessary components for translation from RNA, i.e., ribosomes, tRNA's, aminoacyl tRNA synthases and other factors required for translation; supplementation may be required as is understood in the art, with energy sources, amino acids and other required factors. Starting with the nucleic acids obtained by rolling circle amplification, which is conventionally and most conveniently DNA, means for transcribing the DNA into RNA must also be included. Again, purification by conventional means is performed if needed.

Translation of nucleic acid into protein is well understood in the art, and the foregoing simply alludes to the more common approaches. Modified forms of nucleic acids to the extent they are workable in translation systems may also be used.

The polymeric sequence probe can also be a combination of peptide chain(s) and nucleic acid chain(s). The structure of this probe can also be linear, branched, dendritic, or circular, etc. In one embodiment, the peptide portions function as the recognition site and the nucleic acid portions function as the label sites of the probe. Alternatively, the peptide portions may be the label sites and the nucleic acid portions the recognition sites or various combinations may be employed depending on the complexity of the construction. A spacer sequence may further be added between the recognition sequence and label sequence to avoid steric hindrance. The spacer upstream and downstream of a nucleic acid sequence in the template for translation may contain expression control sequences.

Probes of this type may thus be synthesized by providing a nucleic acid template prepared according to the RCA methods described above and selectively translating those portions of the template that are to be the peptide portions of the probe. Thus, the template is synthesized with certain regions operably linked to expression control sequences which can then effect translation of those portions as described above leaving the remaining portions in the form of nucleic acids. Thus, by taking advantage of the efficiency of the synthesis process in providing complex sequences in nucleic acid templates, complex probes that contain both peptide regions and nucleic acid regions can be readily obtained.

Polymeric sequence probes with branch, dendrite, star, or circular structures can be fabricated by assembling fractions (usually simple structures, such as linear portions).

Linear DNA polymeric sequence probes can be labeled with different fluorophores by incorporating sequences to generate more fluorophore binding regions in the circle, as shown in FIG. 6. The probe made using the circle will have the same number of fluorescence binding sequences (complementary to the circle sequences) repeated. Each segment of fluorescence binding sequence can bind a short oligo bearing a fluorophore. The number of fluorescence tags associated with each short oligo is from 1 to 100, typically 1 to 3. By designing circle sequence and short fluorescent oligos, the amount and ratio of different fluorescence colors can be controlled precisely. The more different sequences are introduced into the circle, the more crosstalk can happen between any members of the assay system. To reduce the crosstalk and further to reduce the assay background, non-natural bases, such as cytidine, guanosine can be incorporated into the short fluorescent oligos to reduce their potential of nonspecific binding to other sequences.

Linear DNA polymeric sequence probes can also be labeled with different fluorophores by adding fluorescent reporter oligos to the primer end of the pre-made long probe for a specific sequence. As shown in FIG. 7, the first long probe contains a primer sequence and a repeating sequence for target 1 capture. The Reporter 1.2 Red (oligo tagged with red fluorophore) and Reporter 1.1 Green (oligo tagged with green fluorophore) can then bind to the long probe from the primer end sequentially. Basically, the two reporters have the complementary sequences but positions are shifted. The different combinations of colors can be used for multiplex detection. For example, the two reporter oligos can be tagged with same or different colors (FIG. 7). By analyzing the ratio of the two colors, different targets can be distinguished.

Branch, star or dendrite DNA polymeric sequence probe can be labeled with different fluorophores. These structures can provide more than one free 3' end for RCA to start with. The number of different circle sequences to be repeated can be one to the number of free 3' end. Each circle sequence can contain one or more than one fluorescence reporter oligo sequences. When the number of free 3' ends equal to 2 and there are no more other ends, the polymeric sequence probe becomes a linear structure, and the same labeling method can be applied.

The polymeric sequence probe can be used for multiplex assays by attaching more than one probe to the target (FIG. 8) instead of attaching one probe. The probes containing different target segment sequences will bind to different positions of the target. In a very small area, different probes line up in a certain sequence, or they have certain ratios of colors, and can be counted as specific target binding. Other configurations of the probes of the invention are shown in FIG. 9 including a star structured probe and a two-armed structure.

Assays

Assays based on the polymeric sequence probe can be carried out both in solution phase and on a support such as a chip or bead surface.

Assays using the polymeric sequence probe carried out in solution require only one binding step. The polymeric sequence probe for use in solution contains recognition sites and multiple labels. An optical signal reading can be carried out by a flow cytometry like system, such as FACS (Fluorescence-activated cell sorting).

Since the signal from the probe itself is identical to the signal from probe-target complex the probe and the probe-target complex must be distinguished. Such distinction can be based on at least one more property of the signal from the probe, such as the diffusion rate of the probe, compared to complex. For example, the diffusion rate of the probe-target complex is much smaller than that of the probe; the signal from the probe can be measured as the function of time, and the change in the diffusion rate can be detected by the detection system such as FCS (fluorescence correlation spectroscopy).

Where more than one probe binds with target, the signals of multiple probes can be detected with the combination of specific intensities, types, colors, and locations. The combinations of the specific signals can be directly detected by detection systems such as optical, electrochemical, electrical, magnetic, chemical, biochemical, piezoelectric sensing system. For example, the optical signals may include the combinations of colors, intensities, types, ratios, locations, and temporal related signals. The specific combination of multiple probes bound to a target gives a unique ratio of different signals such as a color spectrum, which identifies the target as a fingerprint. Multiple different targets can thus be detected simultaneously since each type of target corresponds to a specific combination of signals.

Assays using the polymeric sequence probes can also be carried out on a support such as a chip, bead surface, or well of a microtiter plate. In these assays, a capture probe is immobilized on the surface of the support to capture the target. A polymeric sequence probe binds to the target at a different site of the target and to provide a detectable signal. This is illustrated in FIG. 10. Probes that are not bound to the target are washed away to reduce the background noise. The target molecule can also be captured nonspecifically on the support by electrostatic force, molecule-molecule interactions, or any other binding forces, and then detected with the invention probes.

In one embodiment, the capture probes are first immobilized onto the support and target is then added. After the target molecules are captured by the capture probe, a washing step removes the unbound molecules. The polymeric sequence probes are then added to bind and label the target; after the binding, the excess probes are washed away. An extra labeling step may be required to add tags to the probe if the probe itself does not contain a detectable signal. The extra labeling step is optional if the probe itself provides detectable signal.

Alternatively, the target may first be mixed in solution with the polymeric sequence probe and the resulting complex captured at the surface using a capture reagent. Thus the target molecules or target molecule-containing solution, the polymeric sequence probes and, if needed, the labeling reagents for polymeric sequence probes, can be mixed and added to the support with immobilized capture probe.

In another embodiment, the capture probe, the target molecules or target molecule-containing solution, the polymeric probes, the optional labeling reagents, can be added to the support together.

By binding capture reagents to multiple locations on a solid support, the assays can be designed to detect different targets in the same sample or may be designed to provide an estimate of analyte concentration or both. If a multiplicity of targets is to be detected, a multiplicity of capture reagents is employed, each designed to bind a different target. The various targets can then be distinguished by the location of the binding or may be denoted by alternative labeling of the polymeric sequence probe.

The support itself may be a solid support (such as metal, glass, silicon, silicon dioxide, etc.), polymer support, lipid support or porous support, and may be flat, curved, or variegated.

In general, the assays of the invention can be completed in less than half an hour, with a high signal to noise ratio so that single molecules can be detected, and multiplex assays to detect as many as 10, 100, 1,000, 10,000 or more different targets can be achieved.

Extra tags or the associated architectures added to the polymeric sequence probes such as metal or magnetic particles may induce non-specific binding with non-targeted molecules, species and the environments. This may be minimized by covering or wrapping the probe with polymeric materials. The coverage effectively reduces or removes non-specific binding with the non-targeted molecules and the environmental surfaces, and therefore enhances the sensitivity and specificity of the assay. The polymer wrapping can also protect the polymeric sequence probe from degrading in the in vivo experiment environment, especially when the probe is nucleic acid based.

All of the foregoing formats may be performed using microfluidics, i.e., in fluidic cells or micro/nanofluidic devices.

For surface based assays, microfluidic cells or devices as shown in FIG. 11A have a reaction and reading area where the reaction happens and the signal can be read and measured. The capture probes are immobilized on the surface of the reaction and reading area.

Alternatively, if the reaction is on the surface of beads, the capture probe coupled beads are delivered in to the reaction and reading area through the optional channel shown. The target-containing solution, the reporter probes, and the labeling reagent (optional), can be injected into the reaction and reading area sequentially or simultaneously. During and after the reaction, washing steps can be introduced through the inlets to the outlet.

For solution based assays, the same procedure is used for the reaction. After reaction, the access labeling reagent (usually small molecules) can optionally be washed away by using a filter. However, while washing is optional, it can reduce the background noise for detection, and the size cut-off filter will keep the reporter-target complex in the reaction area during the washing. The complex is then delivered to reading area for signal analysis.

In both surface and solution based assays, temperature control can be applied to the reaction area. Each channel (including inlets, outlets, optional channels, etc.) can be integrated with filters, valves, pumps, etc. The number of different channels can also be varied.

The following examples are intended to illustrate but not limit the invention.

Example 1

Detection of Single-Stranded Target on Solid Substrate

In this example, a capture sequence is coupled through a thiol linkage to a gold pattern on a substrate to capture target analyte from solution, which is then labeled with the invention reagent. The recognition sites on the reagent bind to a different site on the target than the capture probe. The assay is diagrammed in FIG. 11. Concentrations as low as 1 fM can be detected.

Gold spiral patterns on $SiO_2$ substrate were fabricated by photolithography and electron-beam metal deposition, as follows: An $SO_2$ chip was cleaned in piranha bath (30% $H_2O_2$: 98% $H_2SO_4$=1:3) for 10 min, rinsed thoroughly with DI water, and $N_2$ blow dried. 3M™ Adhesive Transfer Tape (467MP) strips were applied to create wells to separate the spiral patterns, so that one well can be used for one sample.

The capture probe oligo is modified with 5' thiol-C6 for attachment to the gold spiral, and the linear DNA to be used to make a circular DNA template for RCA is modified with 5' phosphate so it can be circularized by ligase. The fluorescence-complementary oligo is modified with 5' cy3. The RCA reagents were purchased from EPICENTRE® Biotechnologies.

Oligo sequences are as follows:

```
Capture probe:
                                         (SEQ ID NO: 1)
5' Thiol-Modifier C6-CGAGTACGCCTTCTTGTTGG Linear DNA to be cyclized:
                                         (SEQ ID NO: 2)
5' Phosphate-GAGCAGACAACGAGGACACGTTTTTTTTTTTTT
TTTTTTTTTTTATCGAGCAAGCCATCTGGACCCGTTTTTTTTTTT
```

The linear DNA thus has sequences to generate complements for binding to target and to the fluorescence complementary oligo.

```
Fluorescence complementary oligo:
                                         (SEQ ID NO: 3)
5' cy3-GAGCAGACAACGAGGACACG Primer:
                                         (SEQ ID NO: 4)
AAAAAAAAAAAAAAAAAAAAAAAA Target:
                                         (SEQ ID NO: 5)
GAGCAAGCCATCTGGACCCGCCAACAAGAAGGCGTACTCG
```

Preparation of Polymeric Sequence Probe by RCA

Circular DNA was prepared by ligation followed by excess DNA removal. For ligation, 34 µl sterile water, 2 µl 10 µM linear DNA, 6 µl CircLigase™ II 10× reaction buffer, 3 µl 50 mM $MnCl_2$, 12 µl 5 M Betaine and 3 µl CircLigase™ II polymerase (EPICENTRE® Biotechnologies) were mixed in a 200 µl PCR tube to obtain a total volume of 60 µl, and incubated at 60° C. for 60 min for ligation, then at 80° C. for 10 min to denature the polymerase. After ligation, the excess linear DNA which has not been ligated was removed by adding 1 µl of exonuclease I (EPICENTRE® Biotechnologies) to the 60 µl reaction, and incubated at 37° C. for 90 min for the exonuclease I to digest the linear DNA, then 85° C. for 10 min to denature the exonuclease. The product circle was analyzed by analytical acrylamide gel; circular DNA usually runs slower than linear DNA.

Using the resulting circular DNA, short primer was elongated. 60 µl circular DNA were used in a 480 µl RCA reaction, comprising 60 µl circular DNA, 30 µl RCA primer (40 mM linear DNA), 96 µl 5× RepliPHI™ Phi29 reaction buffer (40 mM Tris-HCl pH 7.5, 50 mM $KCl_2$, and 5 mM $(NH_4)_2SO_4$), 48 µl 10% BSA, 38.4 µl 10 mM dNTP, 19.2 µl 10 unit/µl RepliPHI™ Phi29 DNA polymerase. The reaction was incubated at 37° C. for 1 hr to produce the reagent of the invention. No further purification step is needed.

Use of Reagent to Detect Target

The assay for ssDNA is shown in FIG. 11. To attach the capture probe to substrate, 1 nmole of thiolated capture probe was dissolved in 820 µl tris.HCl 10 mM, NaCl-100 mM TCEP 100 µM solution, and mixed by vortex. 50 µl of the above capture probe solution was added into each well and incubated at room temperature for 30 min, followed by washing and $N_2$ drying. Then 50 µl of SuperBlock™ T20 PBS Blocking Buffer (Pierce) was added into each well, and incubated for 3 min and removed. Solution containing the target at various concentrations was added to each well. After sufficient time for the capture probes to capture target molecules, the solution was removed from the wells, followed by washing 3 times with PBS. 50 µl SuperBlock™ T20 PBS Blocking Buffer was added to each well, and removed after 3 min incubation.

The probe synthesized as described above was added to each well, followed by washing and adding the fluorescence-complementary oligos to tag the long reporter probe. The wells were washed with PBS three times and fluorescence images taken for the wells to quantify the target concentrations (FIG. 12). As shown in FIG. 12, concentrations as low as 1 fM of target could be detected.

Example 2

Detection of Double-Stranded DNA on a Solid Substrate

The same chip was used as in Example 1, and the process is shown in FIG. 13.

To capture the dsDNA (target) on the chip, two capture probes, a sense capture probe and an anti-sense capture probe, were immobilized on the Au surface to capture both strands. The two capture probes target near the 5' end of each strand of the dsDNA, so that once the two strands are captured high energy is applied to re-hybridize them since one strand has to be flipped over. The density of the two capture probes can be controlled in the capture probe immobilization process.

As in Example 1, the capture probe oligos were modified with 5' thiol-C6 to bind to the substrate, and the circular DNA oligos were modified with 5' phosphate. One of the fluorescence complementary oligos is ultimately bound 5' cy3 and the other to 5' 6-FAM.

The relevant oligo sequences are as follows:

```
Sense capture:
                                         (SEQ ID NO: 6)
5' Thiol-Modifier C6-AAAAAAAAAAAAAAATCTCGGCTAGTGC
ATTGTCATAG Anti-sense capture:
                                         (SEQ ID NO: 7)
5' Thiol-Modifier C6-AAAAAAAAAAAAAAAGACCTGAAAGACG
TTATCCACC
```

-continued

Sense circle:
(SEQ ID NO: 8)
5' Phosphate-TTTTTTTTGAGCAGACATTGAGGACAGCTTTTTTTT
TTTTTTTTTTTTTTTTACAAGAAGGCGTACTCGACCTG Anti-sense circle:
(SEQ ID NO: 9)
5' Phosphate-TTTTTTTTTTTTTTTTACGAACACACACGACTACCT
TTTTTTTTTGATCGTCTCGGCTAGTGCTTTTTTTTTTT Sense fluoro-complement:
(SEQ ID NO: 10)
5' cy3-GAGCAGACATTGAGGACAGC Anti-sense fluoro-complement:
(SEQ ID NO: 11)
5' 6 FAM-TACGAACACACACGACTACC Primer:
(SEQ ID NO: 4)
AAAAAAAAAAAAAAAAAAAAAAAA Sense target:
(SEQ ID NO: 12)
ACAAGAAGGCGTACTCGACCTGAAAGACGTTATCCACCATACGGATAGG
GGATCTCAGTACACATCGATCCGGTTCAGCGAGCGGCTCGCCGAGGCAG
GCATCCAACCGTCGGTCGGAGCGGTCGGAAGCTCCTATGACAATGCACT
AGCCGAGACGATC Anti-sense target:
(SEQ ID NO: 13)
GATCGTCTCGGCTAGTGCATTGTCATAGGAGCTTCCGACCGCTCCGACC
GACGGTTGGATGCCTGCCTCGGCGAGCCGCTCGCTGAACCGGATCGATG
TGTACTGAGATCCCCTATCCGTATGGTGGATAACGTCTTTCAGGTCGAG
TACGCCTTCTTGT The dsDNA is first denatured in one of three ways:

A thermal method is performed by heating the dsDNA to 95° C. for 5 min followed by cooling to 60° C. for 5 min then incubating at room temperature for the capture onto the surface. A chemical method is performed by adding 20% formamide, 0.3 M NaOH to dsDNA and reacting for 5 min, followed by adding neutralization buffer to effect capture. Block oligos can also be used. These are short oligos complementary to dsDNA and usually in much higher concentration than the target dsDNA, so that when they bind to the two strands of dsDNA separately, they build steric hindrance to prevent the two strands of dsDNA from hybridizing (FIG. 13, panel 2). Block oligos are usually applied together with thermal or chemical method, especially when the dsDNA is longer than 200 base pairs.

The time for DNA denaturing is short, and statistically, the two strands will not diffuse far away from each other. Therefore, the density of the two capture probes needs to be controlled in the capture probe immobilization process, and the separated strands are captured by the capture probes before they rehybridize.

Once the dsDNA is captured (FIG. 13, panel 3), the same reporting process for ssDNA is used to label the dsDNA (FIG. 13, panels 4 and 5). Only one strand of the dsDNA, may be labeled or both strands may be labeled. Because the two strands have different sequences, they can be labeled by different long reporter probes. Therefore, the two strands can be labeled by either the same dye with complementary oligos or with different dyes.

FIG. 14 shows the fluorescence intensities versus dsDNA target molecule concentrations (100 zM-100 fM, and negative control) using the above assay. It shows the limit of detection for dsDNA is 100 zM, and the dynamic range is larger than seven orders of magnitude.

Example 3

Use of a Solid Core Reporter

A "solid core" can be added to the long reporter probe to provide signal with or without additional labeling. Gold (Au) nanoparticles can provide strong scattering signals and the conjugation chemistry is well developed. An Au nanoparticle is used in this example as the solid core.

The 5' end of the RCA primer is modified with thiol, for reaction with Au to form an S—Au bond. Once the circle binds to the primer, the RCA extension will start in 5'->3' direction.

In this example, the target is double stranded. Two capture probes, sense capture and antisense capture are used. Two different circles are used to make reporter probes: sense circle and anti-sense circle. The two circles use the same primer, which is modified with thiol group for conjugation covalently to the Au nanoparticles as noted above.

The capture probe oligos are also modified with 5' thiol-C6, and the circular DNA oligos are modified with 5' phosphate.

The oligo sequences are as follows:

Sense capture:
(SEQ ID NO: 6)
5' Thiol-Modifier C6-AAAAAAAAAAAAAAATCTCGGCTAGTGC
ATTGTCATAG Anti-sense capture:
(SEQ ID NO: 7)
5' Thiol-Modifier C6-AAAAAAAAAAAAAAAGACCTGAAAGACG
TTATCCACC Sense circle:
(SEQ ID NO: 8)
5' Phosphate-TTTTTTTTGAGCAGACATTGAGGACAGCTTTTTTTT
TTTTTTTTTTTTTTTTACAAGAAGGCGTACTCGACCTG Anti-sense circle:
(SEQ ID NO: 9)
5' Phosphate-TTTTTTTTTTTTTTTTACGAACACACACGACTACCT
TTTTTTTTTGATCGTCTCGGCTAGTGCTTTTTTTTTTT Primer:
(SEQ ID NO: 4)
5' Thiol-Modifier C6-AAAAAAAAAAAAAAAAAAAAAAAA Sense target:
(SEQ ID NO: 12)
ACAAGAAGGCGTACTCGACCTGAAAGACGTTATCCACCATACGGATAGG
GGATCTCAGTACACATCGATCCGGTTCAGCGAGCGGCTCGCCGAGGCAG
GCATCCAACCGTCGGTCGGAGCGGTCGGAAGCTCCTATGACAATGCACT
AGCCGAGACGATC Anti-sense target:
(SEQ ID NO: 13)
GATCGTCTCGGCTAGTGCATTGTCATAGGAGCTTCCGACCGCTCCGACC
GACGGTTGGATGCCTGCCTCGGCGAGCCGCTCGCTGAACCGGATCGATG
TGTACTGAGATCCCCTATCCGTATGGTGGATAACGTCTTTCAGGTCGAG
TACGCCTTCTTGT The density of the thiolated RCA primers on the Au nanoparticles is controlled by the reaction time and salt concentration. The reaction was started with 3 ml Au nanoparticles in 10 mM tris buffer (pH 7.0). 10 µl of 500 µM thiolated RCA primers was added to the Au nanoparticle solution, and incubated on a rotator for 24 hr. Then 1 µl 5M NaCl and 10 µl sodium phosphate buffer were added every 12 hrs for 2 days. The solution was vacuum evaporated (~27° C.) until the final volume decreased to 1 ml. Finally, the Au nanoparticles were washed three times with 1×RCA reaction buffer.

The Au nanoparticle-primer conjugates were then used in the same way as the normal primers, and subjected to RCA as in Example 1. After RCA, the solution was heated to 95° C. for 5 min, and gradually cooled. The Au nanoparticle-long probe conjugates were washed three times in PBS to remove the circles, enzymes and dNTPs.

The Au nanoparticle-long probe conjugates were used as reporters for detection of the sense and antisense targets as in Examples 1 and 2. The results are shown in FIG. 15. No fluorescence complementary oligos are needed for signal reading, since Au nanoparticles can generate strong scattering when close to the Au surface. The scattering signal is imaged and recorded under a darkfield microscope. However, complementary labeled oligos can be coupled to the reporter if desired.

The invention claimed is:

1. A polymeric sequence probe (PSP) for detection of a first target analyte which PSP comprises a macromolecular backbone, along which is disposed a first multiplicity of recognition sites specific for said first target analyte and a multiplicity of labels or label sites wherein at least three of said recognition sites are disposed linearly along said backbone; and wherein said PSP is not bound to analyte and further contains (a) a multiplicity of detectable labels; or
(b) a labeling microparticle or nanoparticle coupled to said macromolecular backbone, or
(c) a combination of a and b; or wherein the macromolecular backbone of said PSP is dendritic or circular; or wherein the macromolecular backbone of said PSP is a protein or a multi-functional organic polymer; or wherein the recognition sites of said PSP are regions of said backbone that are aptamers specific for target analyte; or wherein the recognition sites or label sites are covalently coupled to the macromolecular backbone; or wherein the recognition sites or label sites comprise antibodies or fragments thereof immunospecific for said target analyte; or wherein the recognition sites comprise ligands and the target analyte is a receptor or wherein said recognition sites comprise receptors and the target analyte is a ligand.

2. The polymeric sequence probe of claim 1 wherein further disposed along said backbone is a second multiplicity of recognition sites specific for a second, different target analyte, and
a first and second multiplicity of label sites or labels wherein said first and second label sites or labels are different.

3. The polymeric sequence probe of claim 2 wherein further disposed along said backbone is a third multiplicity of recognition sites specific for a third, different target analyte, and
a first, second and third multiplicity of label sites or labels wherein said first, second and third label sites or labels are different.

4. A polymeric sequence probe for detection of a target analyte which polymeric sequence probe comprises a macromolecular backbone, along which is disposed a first and second multiplicity of label sites or labels wherein said first and second label sites or labels are different, and at least one recognition site.

5. The polymeric sequence probe of claim 1 wherein said PSP is not bound to analyte and further contains
(a) a multiplicity of detectable labels; or
(b) a labeling microparticle or nanoparticle coupled to said macromolecular backbone, or
(c) a combination of a and b.

6. The polymeric sequence probe of claim 1 wherein the macromolecular backbone of said PSP is a protein or a multifunctional organic polymer.

7. The polymeric sequence probe of claim 1 wherein the macromolecular backbone is linear.

8. The polymeric sequence probe of claim 1 wherein the macromolecular backbone of said PSP is dendritic or circular.

9. The polymeric sequence probe of claim 1 wherein said macromolecular backbone is a nucleic acid or a peptide nucleic acid and wherein said recognition sites of said PSP are regions of said backbone that are aptamers specific for target analyte.

10. The polymeric sequence probe of claim 1 wherein the recognition sites or label sites are covalently coupled to the macromolecular backbone.

11. The polymeric sequence probe of claim 1 wherein the recognition sites or label sites comprise antibodies or fragments thereof immunospecific for said target analyte.

12. The polymeric sequence probe of claim 1 wherein the recognition sites comprise ligands and the target analyte is a receptor or wherein said recognition sites comprise receptors and the target analyte is a ligand.

13. The polymeric sequence probe of claim 1 wherein the macromolecular backbone is a polypeptide and wherein said detectable label sites comprise subsequences that bind specifically to detectable label or to moieties coupled to detectable label.

14. The polymeric sequence probe of claim 1 which further includes a microparticle or nanoparticle coupled to the macromolecular backbone.

15. The polymeric sequence probe of claim 14 wherein said nanoparticle is a quantum dot.

16. A method to assay for target analyte which method comprises contacting a sample to be assessed for the presence, absence, or amount of said target analyte with the polymeric sequence probe of claim 1 and detecting the presence, absence, or quantity of probe bound to any target analyte.

17. The method of claim 16 wherein said probe contains a multiplicity of detectable label sites to which label is bound or further contains a microparticle or nanoparticle coupled to said macromolecular backbone or both, and wherein said detecting is of the presence, absence or quantity of label.

18. The method of claim 17 wherein the target analyte is bound to a surface wherein said surface is that of a multiplicity of beads or is that of an article or microtiter plate well.

19. The method of claim 16 which is carried out in solution.

20. The method of claim 19 which is performed in a macrofluidic, microfluidic or nanofluidic device.

21. A method to prepare the polymeric sequence probe of claim 1 that is a nucleic acid which method comprises conducting rolling circle amplification (RCA) of template circular DNA, said circular DNA comprising a separate primer recognizing site and a nucleotide sequence resulting in said recognition site when RCA is conducted,
which method comprises contacting said circular DNA with primer, dNTP's, and reagents for amplification.

22. The method of claim 21, wherein said circular DNA further contains a nucleotide sequence designed to bind to a nucleotide sequence coupled to label.

23. The method of claim 21 wherein said each circular template further contains a sequence that results in one or more detectable label binding sites.

24. The method of claim 21, wherein each single circular DNA comprises nucleotide sequences resulting in multiplicities of at least two different recognition sites when RCA is conducted.

25. The method of claim 21, wherein said different recognition sites bind to different target analytes contained on the same biomolecule or to different biomolecules.

26. A method to prepare the polymeric sequence probe of claim 1 which comprises a peptide, which method comprises translating a nucleic acid template encoding said peptide,
wherein said nucleic acid template is prepared by conducting rolling circle amplification (RCA) of template circular DNA, said circular DNA comprising a separate primer recognizing site and one or more nucleotide sequences resulting in one or more recognition sites and/or one or more label sites when RCA is performed by contacting said circular DNA with primer, dNTP's, and reagents for amplification.

27. The method of claim 26, wherein said template circular DNA further contains one or more nucleotide sequences that results in an expression control sequence in said nucleic acid template.

28. A reagent comprising two or more different labels which is a nucleic acid comprising a double-stranded portion and a single-stranded portion, wherein each strand of the double-stranded portion is labeled with a different label, and wherein the single-stranded portion is complementary to a target nucleic acid analyte.

29. The method of claim 21 which employs at least two circular DNA templates wherein a first circular DNA template comprises a separate primer recognizing site and a nucleotide sequence resulting in a first recognition site and a second circular template comprises a separate primer recognizing site and a nucleotide sequence resulting in a second recognition site.

* * * * *